United States Patent
Minagawa et al.

(10) Patent No.: US 11,360,078 B2
(45) Date of Patent: Jun. 14, 2022

(54) MEDICAL ANALYSIS DEVICE AND CELL ANALYSIS METHOD

(71) Applicants: SUMITOMO RUBBER INDUSTRIES, LTD., Kobe (JP); YAMAGATA UNIVERSITY, Yamagata (JP)

(72) Inventors: Yasuhisa Minagawa, Kobe (JP); Masaru Tanaka, Yonezawa (JP); Takashi Hoshiba, Yonezawa (JP); Tomokazu Shibuya, Yonezawa (JP)

(73) Assignees: SUMITOMO RUBBER INDUSTRIES, LTD., Kobe (JP); YAMAGATA UNIVERSITY, Yamagata (JP)

( * ) Notice: Subject to any disclaimer, the term of this patent is extended or adjusted under 35 U.S.C. 154(b) by 0 days.

(21) Appl. No.: 16/829,714

(22) Filed: Mar. 25, 2020

(65) Prior Publication Data

US 2020/0225212 A1    Jul. 16, 2020

Related U.S. Application Data

(62) Division of application No. 15/692,960, filed on Aug. 31, 2017, now Pat. No. 10,641,760.

(30) Foreign Application Priority Data

Sep. 29, 2016    (JP) .................................. 2016-191616

(51) Int. Cl.
*G01N 33/50*    (2006.01)
*B01L 3/00*    (2006.01)

(52) U.S. Cl.
CPC ........ *G01N 33/5011* (2013.01); *B01L 3/5085* (2013.01); *B01L 3/50855* (2013.01);
(Continued)

(58) Field of Classification Search
CPC ............... B01L 3/50855; B01L 3/5085; G01N 33/5011; C09D 133/14
See application file for complete search history.

(56) References Cited

U.S. PATENT DOCUMENTS

| 5,202,025 A | 4/1993 | Onishi et al. |
|---|---|---|
| 7,211,433 B1 | 5/2007 | Dahm et al. |

(Continued)

FOREIGN PATENT DOCUMENTS

| CN | 104039949 A | 9/2014 |
|---|---|---|
| CN | 105263995 A | 1/2016 |

(Continued)

OTHER PUBLICATIONS

Yao et al., Integr. Biol. (Camb). Apr. 2014, 6(4), 388-398.*
(Continued)

*Primary Examiner* — Vu A Nguyen
(74) *Attorney, Agent, or Firm* — Birch, Stewart, Kolasch & Birch, LLP

(57) ABSTRACT

The present invention provides a medical analysis device and a cell analysis method with which it is possible to count the number of cancer cells, culture the cancer cells, and determine the effect of drugs on the cancer cells. The present invention relates to a medical analysis device intended to capture cancer cells, the medical analysis device having multiple wells.

4 Claims, 3 Drawing Sheets

(52) U.S. Cl.
CPC .... *G01N 33/5005* (2013.01); *B01L 2200/028* (2013.01); *B01L 2300/021* (2013.01); *B01L 2300/0887* (2013.01); *B01L 2300/161* (2013.01); *B01L 2300/165* (2013.01)

(56) References Cited

U.S. PATENT DOCUMENTS

| | | | |
|---|---|---|---|
| 9,372,136 | B2 * | 6/2016 | Kanbara ............... G01N 1/405 |
| 2002/0155617 | A1 | 10/2002 | Pham et al. |
| 2003/0190405 | A1 | 10/2003 | Bowers et al. |
| 2006/0008807 | A1 | 1/2006 | O'Hara et al. |
| 2006/0160066 | A1 | 7/2006 | Bhatia |
| 2008/0008736 | A1 | 1/2008 | Glauser |
| 2009/0186341 | A1 | 7/2009 | Dahm |
| 2010/0261159 | A1 | 10/2010 | Hess |
| 2011/0123414 | A1 | 5/2011 | Ahern et al. |
| 2012/0077246 | A1 | 3/2012 | Hong et al. |
| 2012/0108468 | A1 | 5/2012 | Keselowsky et al. |
| 2012/0156698 | A1 | 6/2012 | Jendoubi |
| 2013/0059288 | A1 | 3/2013 | Dankbar et al. |
| 2013/0071916 | A1 * | 3/2013 | Frutos ............... C09D 189/00 435/289.1 |
| 2013/0072402 | A1 | 3/2013 | Takamura et al. |
| 2013/0210140 | A1 | 8/2013 | Burns et al. |
| 2014/0158604 | A1 | 6/2014 | Chammas et al. |
| 2014/0299539 | A1 | 10/2014 | Takai et al. |
| 2014/0335610 | A1 | 11/2014 | Fukumori et al. |
| 2015/0017221 | A1 | 1/2015 | Hayashi et al. |
| 2015/0285786 | A1 | 10/2015 | Hahn et al. |
| 2016/0011192 | A1 | 1/2016 | Wagner |
| 2016/0069861 | A1 | 3/2016 | Santore et al. |
| 2016/0116477 | A1 | 4/2016 | Hoffmann et al. |
| 2016/0122488 | A1 | 5/2016 | Minagawa |
| 2016/0136552 | A1 | 5/2016 | Nakanishi et al. |
| 2016/0168294 | A1 | 6/2016 | Hayashi et al. |
| 2016/0223521 | A1 | 8/2016 | Okamoto et al. |
| 2016/0291019 | A1 | 10/2016 | Yoon et al. |
| 2017/0113218 | A1 | 4/2017 | Chen et al. |
| 2017/0225166 | A1 | 8/2017 | Toner et al. |
| 2017/0267960 | A1 | 9/2017 | Tsukada et al. |
| 2018/0099105 | A1 | 3/2018 | Minagawa et al. |
| 2018/0201892 | A1 | 7/2018 | Gomi et al. |
| 2019/0048113 | A1 | 2/2019 | Hayashi et al. |
| 2019/0170741 | A1 | 6/2019 | Alix-Panabieres et al. |
| 2019/0233555 | A1 | 8/2019 | Minagawa et al. |
| 2019/0250149 | A1 | 8/2019 | Minagawa et al. |
| 2019/0250151 | A1 | 8/2019 | Minagawa et al. |
| 2020/0056137 | A1 | 2/2020 | Anza et al. |
| 2020/0056138 | A1 | 2/2020 | Anzai et al. |
| 2020/0056154 | A1 | 2/2020 | Anzai et al. |
| 2020/0056155 | A1 | 2/2020 | Anzai et al. |

FOREIGN PATENT DOCUMENTS

| | | |
|---|---|---|
| CN | 105636615 A | 6/2016 |
| EP | 0225703 A2 | 6/1987 |
| EP | 1655354 A2 | 5/2006 |
| EP | 1 905 824 A1 | 4/2008 |
| EP | 2 720 039 A1 | 4/2014 |
| EP | 3244208 A1 | 11/2017 |
| EP | 3301443 A1 | 4/2018 |
| EP | 3301444 A1 | 4/2018 |
| EP | 3527985 A1 | 8/2019 |
| EP | 3527986 A1 | 8/2019 |
| GB | 2472321 A | 2/2011 |
| JP | 2-10160 A | 1/1990 |
| JP | 3-110473 A | 5/1991 |
| JP | 2002-536635 A | 10/2002 |
| JP | 2003-501629 A | 1/2003 |
| JP | 2004-522937 A | 7/2004 |
| JP | 2005-82538 A | 3/2005 |
| JP | 2005-188987 A | 7/2005 |
| JP | 2005-523981 A | 8/2005 |
| JP | 2006-109757 A | 4/2006 |
| JP | 2007-78665 A | 3/2007 |
| JP | 2007-515654 A | 6/2007 |
| JP | 2008-529541 A | 8/2008 |
| JP | 2010-509570 A | 3/2010 |
| JP | 2012-105579 A | 6/2012 |
| JP | 2012-522217 A | 9/2012 |
| JP | 2013-500496 A | 1/2013 |
| JP | 2013-174616 A | 9/2013 |
| JP | 2014-105159 A | 6/2014 |
| JP | 2015-514396 A | 5/2015 |
| JP | 2015-224332 A | 12/2015 |
| JP | 2016-514950 A | 5/2016 |
| JP | 2016-131561 A | 7/2016 |
| JP | 2016-168019 A | 9/2016 |
| JP | 2017-83247 A | 5/2017 |
| JP | 2017-116511 A | 6/2017 |
| JP | 2017-523431 A | 8/2017 |
| JP | 2017-181096 A | 10/2017 |
| JP | 2018-59901 A | 4/2018 |
| WO | WO 99/42608 A1 | 8/1999 |
| WO | WO 00/73794 A2 | 12/2000 |
| WO | WO 02/20825 A1 | 3/2002 |
| WO | WO 03/093357 A1 | 11/2003 |
| WO | WO 2005/064347 A1 | 7/2005 |
| WO | WO 2006/108087 A2 | 10/2006 |
| WO | WO 2007/092028 A2 | 8/2007 |
| WO | WO 2008/057437 A2 | 5/2008 |
| WO | WO 2010/111388 A2 | 9/2010 |
| WO | WO 2011/017094 A2 | 2/2011 |
| WO | WO 2011/157805 A1 | 12/2011 |
| WO | WO 2011/161480 A1 | 12/2011 |
| WO | WO 2012/108087 A1 | 8/2012 |
| WO | WO 2013/112541 A2 | 8/2013 |
| WO | WO 2013/134788 A1 | 9/2013 |
| WO | WO 2014/117021 A2 | 7/2014 |
| WO | WO 2014/203668 A1 | 12/2014 |
| WO | WO 2015/012315 A1 | 1/2015 |
| WO | WO 2015/046557 A1 | 4/2015 |
| WO | WO 2015/137259 A1 | 9/2015 |
| WO | WO 2015/178413 A1 | 11/2015 |
| WO | WO 2016/103002 A1 | 6/2016 |
| WO | WO 2016/115537 A2 | 7/2016 |
| WO | WO-2016115537 A2 * | 7/2016 ....... G01N 35/00029 |
| WO | WO 2017/087032 A1 | 5/2017 |
| WO | WO 2017/178662 A1 | 10/2017 |

OTHER PUBLICATIONS

Yamamura et al., Plos ONE 7(3), 2012, e32370.*
Khoo et al., Oncotarget, vol. 6, No. 17, May 6, 2015, pp. 15578-15593.
Khoo et al., Sci. Adv. 2016, 2: e160074, pp. 1-15.
Yao et al., "Functional analysis of single cells identifies a rare subset of circulating tumor cells with malignant traits", Integr. Biol. (Camb). Apr. 2014, 6(4), pp. 388-398.
Sansyo General Catalogue, "Tissue Culture and Filtration Ware, IWAKI Tissue Culture Ware," 2015, p. 7 (total 2 pages).
"Improved Recovery of Cell-Derived Exosomes by MPC Polymer Coatings," Nippon Genetics Co., Ltd, vol. 9, 2018, with a concise explanation of the relevance.
Fernandez et al., "TP53 mutations detected in circulating tumor cells present in the blood of metastatic triple negative breast cancer patients," Breast Cancer Research, vol. 16, No. 445, 2014, pp. 1-11.
He et al, "Quantitation of Circulating Tumor Cells in Blood Samples from Ovarian and Prostate Cancer Patients Using Tumor-Specific Fluorescent Ligands", International Journal of Cancer, vol. 123, 2008, pp. 1968-1973.
Hoshiba et al., "Blood-compatible poly (2-methoxyethyl acrylate) for the adhesion and proliferation of lung cancer cells toward the isolation and analysis of circulating tumor cells," Journal of Bioactive and Compatible Polymers (2016), vol. 31, No. 4, pp. 361-372.
Hoshiba et al., "Adhesion-Based Simple Capture and Recovery of Circulating Tumor Cells Using a Blood-Compatible and Thermo-Responsive Polymer-Coated Substrate," RSC Advances, vol. 6, 2016 (Published on Sep. 13, 2016), pp. 89103-89112.
Klöckner et al., "Advances in shaking technologies." Trends in Biotechnology, vol. 30, No. 6, Jun. 2012, pp. 307-314.

(56) References Cited

OTHER PUBLICATIONS

Miltenyi Biotec, "Isosation of mononuclear cells from human peripheral blood by density gradient centrifugation," MACS, 2008, pp. 1-2.
Takai, "Bio-interface for Highly Sensitive Blood Analysis Chip," Surface Science, vol. 32, No. 9, 2011, pp. 575-580, with English abstract.
Vona et al., "Isolation by Size of Epithelial Tumor Cells, A New Method for the Immunomorphological and Molecular Characterization of Circulating Tumor Cells," American Journal of Pathology, vol. 156, No. 1, Jan. 2000, pp. 57-63.
Williams, "Circulating Tumor Cells," PNAS, vol. 110, No. 13, Mar. 26, 2013, pp. 4861.
Xu et al., "Optimization and Evaluation of a Novel Size Based Circulating Tumor Cell Isolation System," PLOS One, Sep. 23, 2015, pp. 1-23.
Gach et al., "Micropallet Arrays for the Capture, Isolation and Culture of Circulating Tumor Cells From Whole Blood of Mice Engrafted With Primary Human Pancreatic Adenocarcinoma", Biosensors and Bioelectronics, vol. 54, 2014, (Available online Nov. 18, 2013), pp. 476-483.

\* cited by examiner

A-A cross-sectional view

MEDICAL ANALYSIS DEVICE AND CELL ANALYSIS METHOD

CROSS-REFERENCE TO RELATED APPLICATIONS

This application is a Divisional of copending Application Ser. No. 15/692,960, filed on Aug. 31, 2017, which claims priority under 35 U.S.C. § 119(a) to Application No. 2016-191616, filed in Japan on Sep. 29, 2016, all of which are hereby expressly incorporated by reference into the present application.

TECHNICAL FIELD

The present invention relates to a medical analysis device and a cell analysis method which can capture blood cells or cancer cells present in blood or biological fluid.

BACKGROUND ART

When cancer cells are formed, they are known to appear in due course in blood and biological fluid. Such cancer cells in blood are called "circulating tumor cells (CTCs)". Thus, it is expected that the circulating tumor cells can be examined, e.g., to confirm the cancer-treating effect, predict prognosis life expectancy, predict the effect of anticancer drugs before administration, or examine treatment methods through genetic analysis of cancer cells.

However, a problem exists in that since the number of circulating tumor cells is very small (several to hundreds of cells/1 mL of blood), such cancer cells are difficult to capture.

For example, the CellSearch System is known as a technique for capturing circulating tumor cells. This technique, which utilizes an antigen-antibody reaction (capture by EpCAM antibody), can only capture cancer cells expressing EpCAM, and the types of capturable cancer cells are limited.

CITATION LIST

Patent Literature

Patent Literature 1: JP 2005-523981 T

SUMMARY OF INVENTION

Technical Problem

The present invention aims to solve the above problem and provide a medical analysis device and a cell analysis method with which it is possible to count the number of cancer cells, culture the cancer cells, and determine the effect of drugs on the cancer cells.

Solution to Problem

The present invention relates to a medical analysis device, intended to capture cancer cells, the medical analysis device having multiple wells.

The multiple wells are preferably separable.
The multiple wells are preferably arranged in matrix form.
Each of the multiple wells preferably has its own identification to determine where it is located.
Each well preferably has a hydrophilic polymer layer formed at least partly on an inner surface thereof.

The hydrophilic polymer layer is preferably formed of at least one hydrophilic polymer selected from the group consisting of poly(meth)acryloylmorpholine and a polymer represented by the following formula (I):

$$\text{(I)}$$

wherein $R^1$ represents a hydrogen atom or a methyl group, $R^2$ represents an alkyl group, m represents 1 to 5, and n represents the number of repetitions.

The hydrophilic polymer layer is preferably formed of a copolymer of at least one hydrophilic monomer selected from the group consisting of (meth)acryloylmorpholine and a compound represented by the following formula (I-1):

$$\text{(I-1)}$$

wherein $R^1$, $R^2$, and m are as defined above, with a second monomer.

The present invention also relates to a cell analysis method, including introducing a blood or biological fluid test sample into multiple wells of the medical analysis device described above to capture cancer cells, and then counting the number of cancer cells in the blood or biological fluid test sample in at least one of the multiple wells.

The cell analysis method preferably includes increasing the number of cancer cells by culturing in the wells that are not used to count the number of cancer cells, and then determining an effect of a drug on the cancer cells.

Advantageous Effects of Invention

Since the medical analysis device intended to capture cancer cells according to the present invention has multiple wells, the multiple wells can be separated into wells for counting the number of captured cancer cells and for culturing the cancer cells. Accordingly, even when a reagent that damages cells is used in the wells for counting the number of cancer cells, the separated wells for culturing cancer cells are not affected by the reagent, and it is therefore possible to count the number of captured cancer cells and culture the cancer cells. Thus, for example, it is possible to sufficiently capture cancer cells from blood or biological fluid to count the number of cancer cells, and at the same time to culture the captured cancer cells without damaging the cancer cells. Further, the cultured cancer cells can be used to determine the effect of drugs such as anticancer drugs ex vivo before administration and screen the drugs.

DESCRIPTION OF EMBODIMENTS

The present invention relates to a medical analysis device intended to capture cancer cells, having multiple wells.

Since multiple wells are provided, they can be separated into wells for counting the number of cancer cells and for culturing cancer cells. Thus, for example, the following method can be used: the presence or absence of cancer cells is first confirmed in wells for counting, and if the presence is confirmed, the cancer cells are cultured in wells for culturing and then used to determine the effect of drugs.

Moreover, for example, when a hydrophilic polymer layer is formed on the inner surface of the wells, the ability to capture many types of cancer cells, including cancer cells not expressing EpCAM, is greatly improved while reducing the ability to capture platelets and others, as compared to when no hydrophilic polymer layer is formed. This has a significant effect in selectively capturing cancer cells. Thus, it is possible to sufficiently capture cancer cells from blood or biological fluid while reducing the adhesion or attachment of other proteins or cells, thereby selectively capturing the cancer cells. Accordingly, the present invention can be suitably used to confirm the presence or absence of cancer cells, culture the cancer cells, and determine the effect of drugs thereon.

Examples of preferred embodiments of the present invention are described below with reference to drawings.

Figure 1:
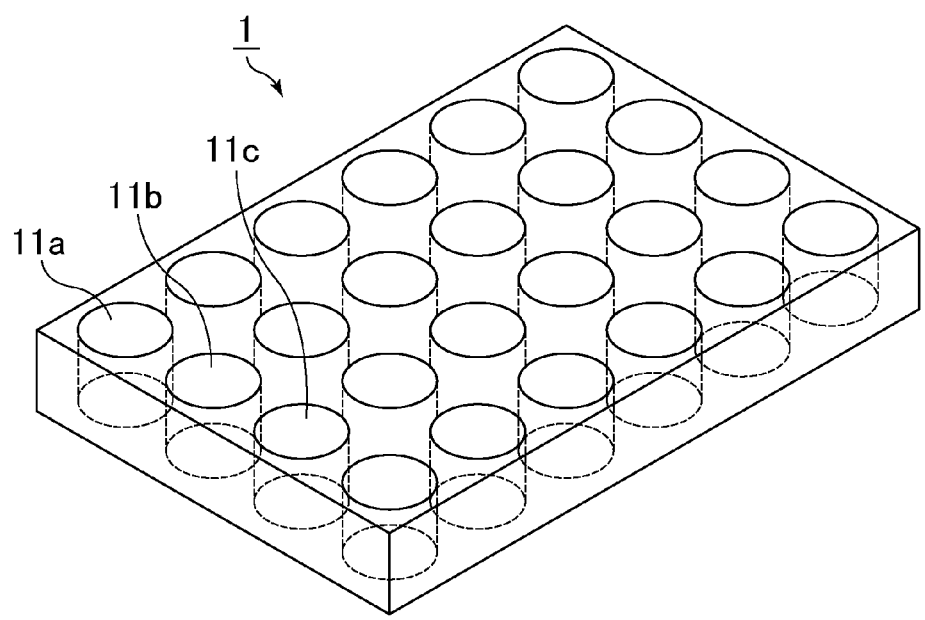
FIG. 1 is an exemplary schematic view of a multi-well plate (medical analysis device) having multiple wells.

A medical analysis device 1 (multi-well plate 1) illustrated in FIG. 1 is a device intended to capture cancer cells in which wells 11 (wells 11a, 11b, 11c, etc.) are arranged in so-called matrix form. The multi-well plate 1 has multiple wells 11 having a circular opening. The wells 11, which are recesses into which blood, biological fluid, or the like is injected, can be used to confirm the presence or absence of cancer cells in the injected blood or biological fluid, count the number of cancer cells, culture the cancer cells, determine the effect of drugs, and screen the drugs.

Although FIG. 1 shows a 24-well plate having 24 wells 11 arranged in 4 rows by 6 columns as an example, it is sufficient for the multi-well plate 1 to have at least two wells 11, and any number of wells 11 may be provided. Examples other than the 24-well plate include general multi-well plates in which the number of wells 11 is 6, 96, 384, etc.

Examples of the material of the multi-well plate 1 include acrylic resins (polyacrylic resins) such as polymethyl acrylate, polymethyl methacrylate, polyacrylic acid, and polymethacrylic acid, cycloolefin resins (polycycloolefins), carbonate resins (polycarbonates), styrene resins (polystyrenes), polyester resins such as polyethylene terephthalate (PET), and polydimethylsiloxanes.

Each well 11 is a non-through hole which is opened at the surface of the multi-well plate 1. Blood or biological fluid is injected into the wells 11 through the respective openings. If the presence of cancer cells is confirmed, a culture fluid for culturing the cancer cells is also injected.

The diameter R and depth D of the opening of each well 11 are not particularly limited, and may be those of a conventional multi-well plate 1. Although in FIG. 1, the inner side surface of each well 11 is substantially vertical to the opposite sides of the multi-well plate 1, the inner side surface of each well 11 may be inclined to taper from the opening to the bottom. Alternatively, the inner side surface may be inclined to flare out from the opening to the bottom.

Though the wells 11 in FIG. 1 are circularly opened, the opening of the wells 11 may be of any shape such as a quadrangle.

Figure 2A:
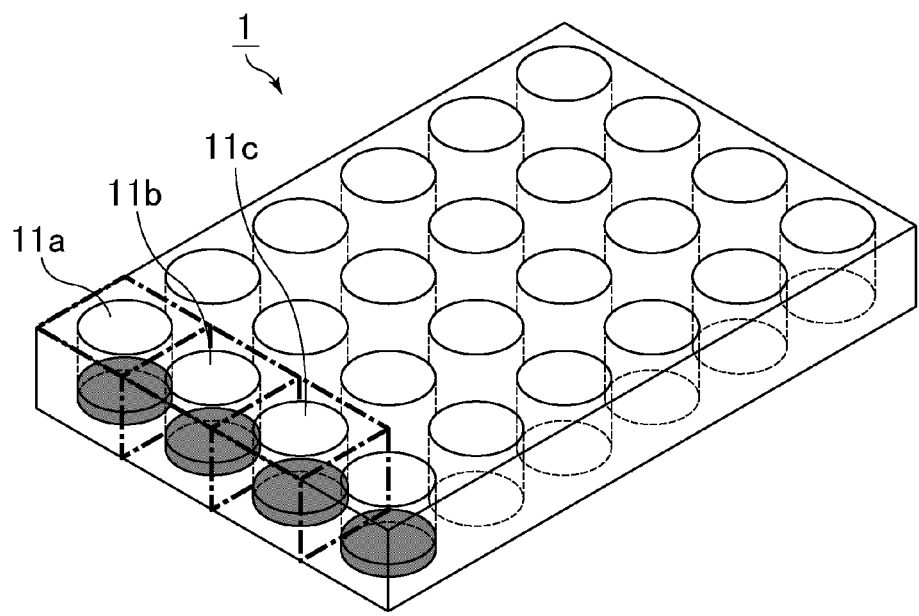
FIGS. 2A-2C are an exemplary schematic view of three wells 11a, 11b, and 11c which are used separately from each other.
Figure 2B:
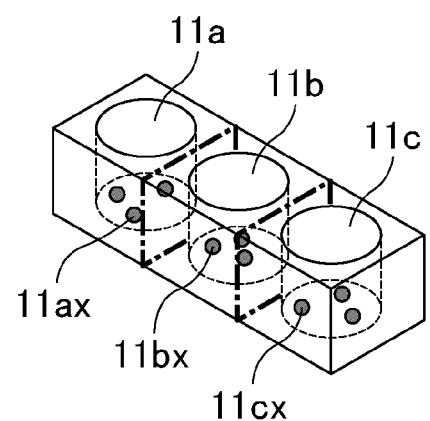
Figure 2C:
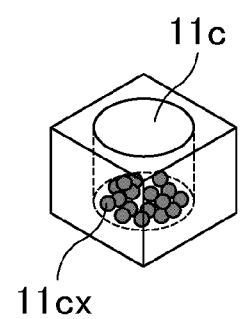

The multi-well plate 1 may suitably be one in which the multiple wells 11 are separable. FIGS. 2A-2C are an exemplary schematic view of separable three wells 11a, 11b, and 11c which are used separately from each other.

Firstly, blood from a patient is injected into the wells 11a, 11b, and 11c to allow cancer cells to adhere to the wells, and then the wells 11a, 11b, and 11c are separated from each other. Next, two wells including wells 11a and 11b (wells for counting the number of cancer cells) are used to confirm the presence or absence of cancer cells and count the number of cancer cells. The number of cancer cells 11ax in the well 11a is first counted, and if the number of cancer cells is small, the number of cancer cells 11bx in the well 11b is counted again. If at least a predetermined number of cancer cells are observed, the cancer cells 11cx in the well 11c (well for culturing cancer cells) are cultured. The increased number of cancer cells 11cx obtained by culturing can be used, e.g., to determine the effect of drugs such as anticancer drugs and screen the anticancer drugs. The wells may be separated by known means that can separate the wells.

Each of the multiple wells 11 may suitably have its own identification to determine where it is located. In this case, even after the wells are separated, wells into which the same blood or biological fluid is injected can be easily recognized. The identification may be carried out, for example, by addition of an identifier. The identifier may be in any form, and examples include characters, numbers, figures such as polygons, arrows, lines (bars), dots, and bar codes such as QR Code®.

Figure 3A:
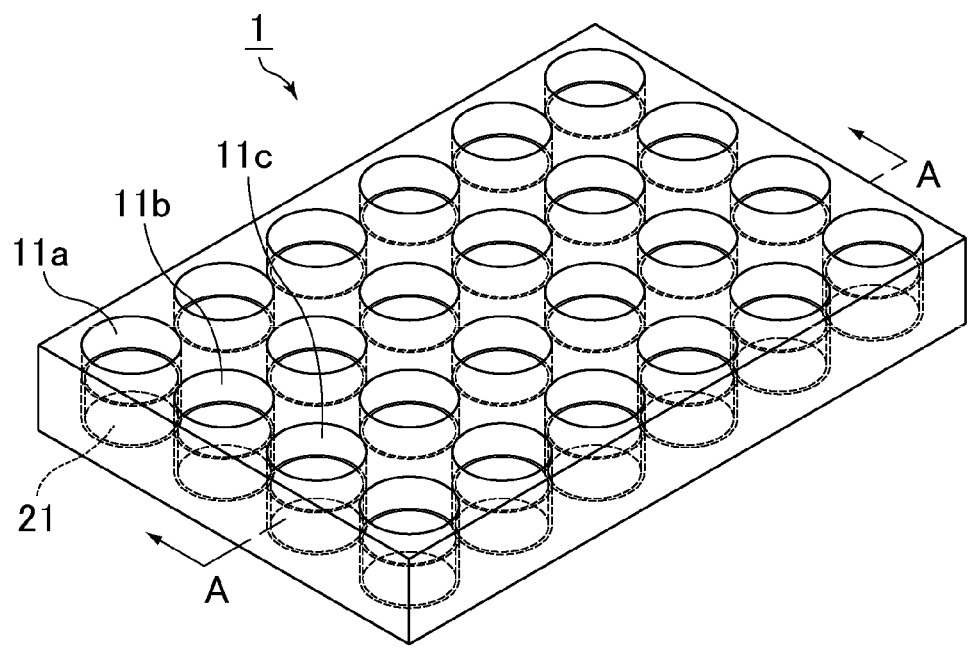
FIGS. 3A and 3B are an exemplary schematic view of a multi-well plate (medical analysis device) having multiple wells with a hydrophilic polymer layer formed thereon.
Figure 3B:
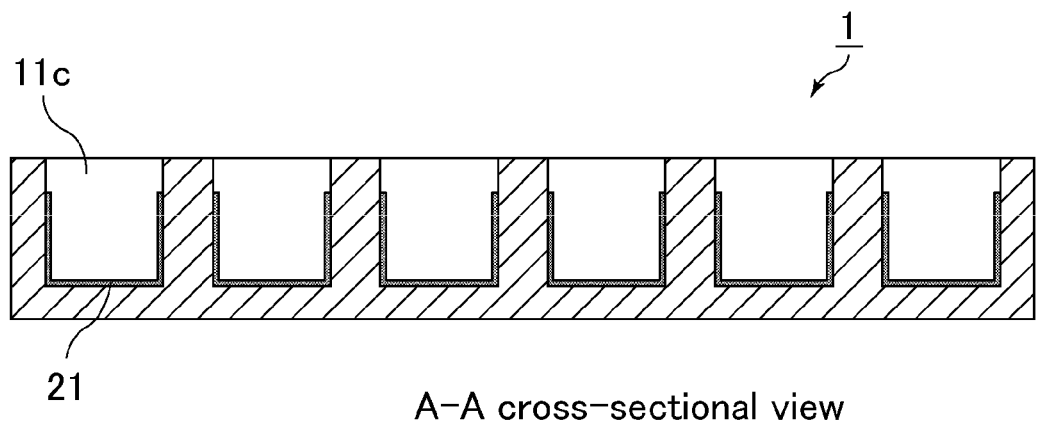

In the multi-well plate 1 (medical analysis device 1), each well 11 preferably has a hydrophilic polymer layer formed at least partly on the inner surface thereof. FIGS. 3A and 3B illustrate a case where a hydrophilic polymer layer 21 is formed on the bottom surface and a part of the side surface of the wells.

Once blood or biological fluid is introduced into the wells 11, cancer cells present in the blood or biological fluid are adsorbed onto the hydrophilic polymer layer 21, while the adsorption of platelets, erythrocytes, and the like is reduced. Accordingly, cancer cells can be adsorbed onto the hydrophilic polymer layer 21 by introducing and retaining blood or biological fluid in the wells 11 for a predetermined time, followed by washing. Then, the number of adsorbed cancer cells is counted to determine the number of cancer cells in the blood or biological fluid, which can be expected to be useful e.g. for confirming the cancer-treating effect.

The thickness of the hydrophilic polymer layer 21 (layer formed of a hydrophilic polymer) is preferably 2 to 200 nm, more preferably 20 to 180 nm. When the thickness is adjusted within the range indicated above, low adsorption of proteins and cells and selective adsorption or adhesion of cancer cells can be well achieved.

The hydrophilic polymer may be appropriately selected from polymers having hydrophilicity. For example, it may be a homopolymer or copolymer of one or two or more hydrophilic monomers, or a copolymer of one or two or more hydrophilic monomers with a second monomer. Examples of the homopolymer and copolymers include polyacrylic acid, polyacrylic acid esters, polymethacrylic acid, polymethacrylic acid esters, polyacryloylmorpholine, polymethacryloylmorpholine, polyacrylamide, and poly methacrylamide.

The hydrophilic monomer may be any monomer containing a hydrophilic group. Examples of the hydrophilic group include known hydrophilic groups such as an amide group, a sulfuric acid group, a sulfonic acid group, a carboxylic acid group, a hydroxy group, an amino group, and an oxyethylene group.

Specific examples of the hydrophilic monomer include (meth)acrylic acid, (meth)acrylic acid esters (e.g. alkoxyalkyl (meth)acrylates such as methoxyethyl (meth)acrylate, and hydroxyalkyl (meth)acrylates such as hydroxyethyl (meth)acrylate), (meth)acrylamide, and (meth)acrylamide derivatives containing cyclic groups (e.g. (meth)acryloylmorpholine).

The second monomer may be appropriately selected as long as it does not inhibit the effect of the hydrophilic polymer. Examples include aromatic monomers such as styrene, vinyl acetate, and N-isopropylacrylamide which can impart temperature responsiveness.

In particular, the hydrophilic polymer is preferably at least one selected from the group consisting of poly(meth)acryloylmorpholine and a polymer represented by the following formula (I):

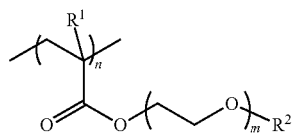

(I)

wherein $R^1$ represents a hydrogen atom or a methyl group, $R^2$ represents an alkyl group, m represents 1 to 5, and n represents the number of repetitions.

The alkyl group represented by $R^2$ preferably has a carbon number of 1 to 10, more preferably 1 to 5. In particular, $R^2$ is particularly preferably a methyl group or an ethyl group. The symbol m is preferably 1 to 3, while n (number of repeating units) is preferably 15 to 1,000, more preferably 30 to 500.

Alternatively, the hydrophilic polymer may also suitably be a copolymer of at least one hydrophilic monomer selected from the group consisting of (meth)acryloylmorpholine and a compound represented by the following formula (I-1):

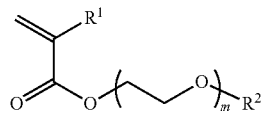

(I-1)

wherein $R^1$, $R^2$, and m are as defined above,
with a second monomer.

From the standpoint of selective adsorption or adhesion to cancer cells, the hydrophilic polymer preferably has a weight average molecular weight (Mw) of 4,000 to 150,000, more preferably 5,000 to 100,000, still more preferably 8,000 to 50,000. Mw as used herein can be determined by gel permeation chromatography (GPC) (GPC-8000 series produced by TOSOH Corporation, detector: differential refractometer, column: TSKGEL SUPERMULTIPORE HZ-M produced by TOSOH Corporation) calibrated with polystyrene standards.

The medical analysis device of the present invention can be produced, for example, by preparing a multi-well plate 1 including multiple wells 11 as illustrated in FIGS. 1 to 3B, optionally followed by addition of other members (parts).

Specifically, when it is desired to produce a multi-well plate 1 with a hydrophilic polymer layer 21 formed thereon, the multi-well plate 1 with a polymer layer formed of a hydrophilic polymer can be produced by dissolving or dispersing a hydrophilic polymer in any solvent to prepare a hydrophilic polymer solution or dispersion, and entirely or partially coating the inner surface of each well 11 with the hydrophilic polymer solution or dispersion by a known method, such as (1) by injecting the hydrophilic polymer solution or dispersion into the wells 11, and retaining it for a predetermined time, or (2) by applying (spraying) the hydrophilic polymer solution or dispersion to the inner surface of the wells 11. Then, other parts, if necessary, are added to the prepared multi-well plate 1, whereby a medical analysis device can be produced.

The solvent, injection method, application (spraying) method, and other conditions may be conventionally known materials or methods.

The retention time in the method (1) or (2) may be selected appropriately according to the size of the wells 11, the type of liquid introduced, and other factors, and is preferably five minutes to ten hours, more preferably ten minutes to five hours, still more preferably 15 minutes to two hours. After the retention, the excess hydrophilic polymer solution or dispersion may be discharged followed by drying, as required.

The cell analysis method of the present invention includes introducing a blood or biological fluid test sample into multiple wells of the medical analysis device described above to capture cancer cells, and then counting the number of cancer cells in the blood or biological fluid test sample in at least one of the multiple wells. Thus, since the multiple wells can be separated into wells for counting the number of cancer cells and for culturing cancer cells, it is also possible to increase the number of cancer cells by culturing in the wells that are not used to count the number of cancer cells, and then determine the effect of drugs on the cancer cells.

EXAMPLES

The present invention is specifically described with reference to examples below, but is not limited only thereto.

Example 1

2-methoxyethyl acrylate was thermally polymerized at 80° C. for six hours using azobisisobutyronitrile (AIBN) to produce poly(2-methoxyethyl acrylate) (molecular weight Mn: about 15,000, Mw: about 50,000). Then, a 2.5 w/v % solution of the poly(2-methoxyethyl acrylate) in methanol was prepared.

The poly(2-methoxyethyl acrylate) solution (2.5 w/v %) was injected into a polystyrene analysis device having three wells, and left for 30 minutes at room temperature. Thereafter, the solution was drawn using a pipette, followed by drying to prepare an analysis device including a multi-well plate with a hydrophilic polymer layer (poly(2-methoxyethyl acrylate) layer: 88 nm) formed thereon as illustrated in FIGS. 3A and 3B.

(Counting of the Number of Cancer Cells and Culturing of Cancer Cells)

Fibrosarcoma (HT-1080) was suspended in a dissociation solution and a portion of the suspension was resuspended in phosphate buffered saline (PBS solution) to count the number of cells using a blood cell counter. Using the obtained number, the dissociation solution containing fibrosarcoma (HT-1080) was resuspended in blood so that the calculated plating density (concentration) was 2,850 cells/cm$^2$.

A 1 ml portion of this blood suspension was injected into each well of the analysis device and left at 37° C. for one hour to cause adhesion. Then, non-adherent cells were washed away with a PBS solution. The wells were separated from each other, and two wells were subjected to immunostaining to count the number of cancer cells using a fluorescence microscope. The HT1080 cell count for the well 1 was 1,560 cells/cm$^2$, while the HT1080 cell count for the well 2 was 1,380 cells/cm$^2$.

Accordingly, a culture medium was put in the separate well 3, followed by culturing at 37° C. for two days. The well 3 showed considerable cell growth and colony formation was observed.

The results demonstrated that the present analysis device can be used to selectively capture cancer cells from blood or biological fluid to count the number of cancer cells; culture the captured cancer cells without damaging the cancer cells; and determine the effect of drugs such as anticancer drugs on the cultured cells ex vivo before administration and screen the drugs.

REFERENCE SIGNS LIST

1: Medical analysis device (Multi-well plate)
11, 11a, 11b, 11c: Well
11ax, 11bx, 11cx: Cancer cell
21: Hydrophilic polymer layer

The invention claimed is:

1. A medical analysis device, intended to capture cancer cells,
   the medical analysis device comprising multiple wells,
   wherein the medical analysis device is made of polystyrene, and
   wherein each well has a hydrophilic polymer layer formed at least partly on an inner surface thereof, and
   wherein the hydrophilic polymer layer is formed of at least one selected from the group consisting of
   (a) poly(meth)acryloylmorpholine,
   (b) a polymer represented by the following formula (I):

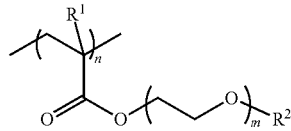

wherein R$^1$ represents a hydrogen atom or a methyl group, R$^2$ represents an alkyl group, m represents 1 to 5, and n represents the number of repetitions, and
   (c) a copolymer of at least one hydrophilic monomer selected from the group consisting of (meth)acryloylmorpholine and a compound represented by the following formula (I-1):

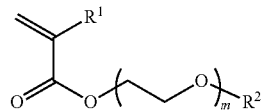

wherein R$^1$ of formula (I-1) represents a hydrogen atom or a methyl group, R$^2$ represents an alkyl group, and m represents 1 to 5,
   with a second monomer.

2. The medical analysis device according to claim 1, wherein the multiple wells are separable.

3. The medical analysis device according to claim 1, wherein the multiple wells are arranged in matrix form.

4. The medical analysis device according to claim 1, wherein each of the multiple wells has its own identification to determine where it is located.

* * * * *